United States Patent [19]

Ohorodnik et al.

[11] 4,318,865
[45] Mar. 9, 1982

[54] PRODUCTION OF 2-CHLOROFORMYLETHYLMETHYLPHOSPHINIC ACID CHLORIDES

[75] Inventors: Alexander Ohorodnik, Erftstadt; Hubert Neumaier, Brühl; Klaus Gehrmann, Erftstadt, all of Fed. Rep. of Germany

[73] Assignee: Hoechst Aktiengesellschaft, Frankfurt am Main, Fed. Rep. of Germany

[21] Appl. No.: 185,154

[22] Filed: Sep. 8, 1980

[30] Foreign Application Priority Data

Sep. 11, 1979 [DE] Fed. Rep. of Germany ....... 2936609

[51] Int. Cl.³ .............................................. C07F 9/34
[52] U.S. Cl. .................................................. 260/543 P
[58] Field of Search ..................................... 260/543 P

[56] References Cited

U.S. PATENT DOCUMENTS

| | | | |
|---|---|---|---|
| 4,022,826 | 5/1977 | Lohmar et al. | 260/543 P |
| 4,042,888 | 12/1977 | Ohorodnik et al. | 260/543 P |
| 4,101,573 | 7/1978 | Gehrmann et al. | 260/543 P |
| 4,104,304 | 8/1978 | Schafer et al. | 260/543 P |

OTHER PUBLICATIONS

Khairullin, V. K. et al. *Chemical Abstracts*, vol. 69 (1968) #106,816k.
Rehberg, C. E. et al. *J. Am. Chem. Socisty*, vol. 67 (1945) pp. 208–210.

*Primary Examiner*—Natalie Trousof
*Assistant Examiner*—L. Hendriksen
*Attorney, Agent, or Firm*—Connolly and Hutz

[57] ABSTRACT

The invention relates to a process for making 2-chloroformylethylmethylphosphinic acid chlorides of the general formula:

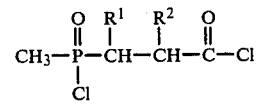

in which $R^1$ and $R^2$ each stand for hydrogen or $CH_3$. To this end, methyldichlorophosphane is reacted with acrylic acid, methacrylic acid or crotonic acid at elevated temperature. More particularly, a solution of methyldichlorophosphane in phosphorus trichloride, the solution originating from a reaction of phosphorus trichloride with methane at temperature higher than 500° C., is used. The reaction is effected at temperatures ithin the range 50° to 90° C. in the presence of hydrogen chloride; and the phosphorus trichloride is distilled off.

6 Claims, No Drawings

PRODUCTION OF 2-CHLOROFORMYLETHYLMETHYLPHOSPHINIC ACID CHLORIDES

It has been described that 2-chloroformylethylmethylphosphonic acid chloride can be made by reacting methyldichlorophosphone with acrylic acid. Khairullin et al. (Z. Obsc. Chim. 37, 710–714 (1967)), for example, disclosed the preparation at temperatures lower than 36° C. with subsequent distillation of the compound which was obtained in a yield of 72% of the theoretical.

During the reaction, 138.5 kj heat is set free per mol of 2-chloroformylethylmethyl-phosphinic acid chloride. This fact makes it necessary for the reaction to be carried out over long periods at low temperatures in order to avoid decomposition of the thermally unstable reaction products. It has, however, not been possible heretofore to inhibit by-product formation to an extent whereby the subsequent distillative purification of the reaction products would have been rendered unnecessary. In addition to this, the substance and space/-timeyields obtained heretofore have been commercially unattractive.

A process which avoids the above difficulties has been described in German Pat. No. 2 529 731 which provides for 2-chloroformylethylmethyl-phosphinic acid chloride to be made continuously, for example, by reacting methyldichlorophosphane with acrylic acid at 50°–120° C. In this process, the reaction heat is easy to abstract and desirable product is obtained in very good yields and with high purity.

Despite this, the process just described is not fully satisfactory inasmuch as pure methyldichlorophosphane has to be used therein as starting material. As disclosed in Belgian Pat. No. 856 773, for example, methyldichlorophosphane is obtained by reacting phosphorus trichloride with methane at temperatures higher than 500° C., the resulting crude product containing 15 to 20 weight% of methyldichlorophosphane, the balance being predominantly phosphorus trichloride. The recovery of pure methyldichlorophosphane from the methyldichlorophosphane/phosphorus trichloride mixture as described in Belgian Pat. No. 857 203 entails considerable expenditure of apparatus and energy.

The present invention now unexpectedly provides a process for making 2-chloroformylethylmethyl-phosphinic acid chlorides of the general formula:

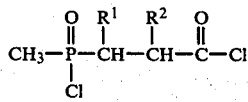

wherein methyldichlorophosphane is reacted with an α,β-unsaturated acid of the general formula:

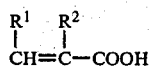

in which formulae $R^1$ and $R^2$ each stand for H or $CH_3$. The process, which permits the chlorides to be produced selectively in very good substance and space/-time-yields, comprises effecting the reaction at temperatures within the range 50° to 90° C. in the presence of hydrogen chloride.

This is a completely unexpected result inasmuch as it has long been known to the artisan that phosphorus trichloride undergoes reaction at about 60° C., e.g. with acrylic acid to give acrylic acid chloride which in turn can be converted with hydrogen chloride to β-chloropropionic acid chloride (cf. Rehberg, Dixon and Fisher, Journ. Amer. Chem. Soc. 67, 209 (1945)).

The invention provides for the present process to be carried out continuously or discontinuously. The reaction proceeds very rapidly and is terminated within about 0.2 to 3 hours in a customary apparatus, depending on the dimensions of the latter and the reaction temperature selected. It is preferable for the reaction to be effected continuously inasmuch as the reaction heat is easy to abstract and the reaction itself occurs rapidly with high conversion rates and good space/time-yields.

In the event of the process being effected batch-wise, the invention provides for a stream of hydrogen chloride gas to be passed through a reactor so as to establish a hydrogen chloride gas atmosphere therein, for the reactor to be fed with a solution of methyl-dichlorophosphane in phosphorus trichloride, for the solution to be heated to a desirable temperature and admixed with metered proportions of the α,β-unsaturated carboxylic acid, the temperature being maintained. The quantity of hydrogen chloride gas used is not critical.

In the event of the process being effected continuously, it is good practice to introduce the methyldichlorophosphane/phosphorus trichloride-solution and α,β-unsaturated carboxylic acid in the necessary quantitative ratio and at the desirable temperature into a heatable circulation reactor and to pass a stream of hydrogen chloride through the reaction mixture. Once again, the quantity of hydrogen chloride gas used is not critical. Reaction product is taken from the reactor at the same rate as feed components are admitted thereto.

A preferred feature provides for the present reaction to be carried out at temperatures within the range 70° to 76° C. A particularly advantageous feature provides for the present reaction to be effected at the boiling point of the reaction mixture; in this case, a portion of reaction heat can be abstracted in simple manner by vapor cooling.

It is also good practice to use the methyldichlorophosphane reactant and α,β-unsaturated carboxylic acid reactant in a molar ratio within the range 1:0.8–1.2. The yield, based on methyldichlorophosphane, is not adversely affected by the use of an excess of α,β-unsaturated carboxylic acid. On the other hand however, the unsaturated acid in excess undergoes reaction, and is consumed thereby, with the large excess of phosphorus trichloride. As a result, the yield, based on the carboxylic acid, is reduced and undesirable by-products are being formed. Preference should therefore be given to the use of a slight deficiency, based on the stoichiometric quantity of the α,β-unsaturated carboxylic acid. In this event, a minor quantity of methyldichlorophosphane remains unreacted which, however, is recovered together with phosphorus trichloride during distillation of low-boiling matter, and can be recycled, in the form of distillate, to the apparatus used for making methyldichlorophosphane from phosphorus trichloride and methane.

The process of the present invention permits the reaction product to be freed from low-boiling fractions comprised predominantly of phosphorus trichloride and minor proportions of unreacted methyldichlorophosphane, if any, by simple distillative treatment until establishment of a temperature of 120° to 140° C. in the residue. The distillation can be effected at atmospheric pressure or under vacuum, discontinuously e.g. in a distilling apparatus provided with a distillation bridge and descending cooler, or continuously in a circulation evaporator provided with a splash shield and descending cooler. It is preferable, however, to effect the distillation continuously under atmospheric pressure, high-boiling residue being in this event circulated through the evaporator by means of a stripping gas.

The residue, which is 2-chloroformylethylmethylphosphinic acid chloride need not be purified, but can directly be reacted in known manner, e.g. as described in German Pat. No. 2 531 238, with acetic anhydride to give 2-methyl-2,5-dioxo-1-oxa-2-phospholane. Compounds of this nature are very useful for condensation into polyester material. Filaments, fibers, films or moulded articles made therefrom can thereby be given very good flame-retardant or self-extinguishing properties. Needless to say, it is necessary for the 2-chloroformyl-ethylmethylphosphinic acid chlorides to be very pure in order to avoid adverse effects on the various quality-defining characteristics of materials rendered flame-retardant therewith.

The present invention relates more particularly to a process for making 2-chloroformylethylmethylphosphinic acid chlorides of the general formula:

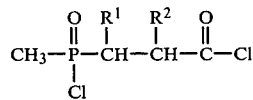

in which $R^1$ and $R^2$ each stand for hydrogen or $CH_3$, by reacting methyldichlorophosphane with acrylic acid, methacrylic acid or crotonic acid at elevated temperature, which comprises: using a solution of methyldichlorophosphane in phosphorus trichloride, the solution originating from a reaction of phosphorus trichloride with methane at temperatures higher than 500° C.; effecting the reaction at temperatures within the range 50° to 90° C. in the presence of hydrogen chloride; and distilling off the phosphorus trichloride.

Preferred features of the present invention provide:
(a) for the methyldichlorophosphane solution in phosphorus trichloride to contain 5 to 95 weight%, preferably 10 to 25 weight%, of methyldichlorophosphane;
(b) for 0.01 to 1 mol, preferably 0.05 to 0.5 mol, of hydrogen chloride to be passed through the reaction mixture per mol of methyldichlorophosphane per hour;
(c) for the reaction to be effected at temperatures within the range 70° to 76° C.;
(d) for methyldichlorophosphane and α,β-unsaturated carboxylic acid to be used in a molar ratio of 1:0.8–1.2, preferably 1:0.95–1.05; and
(e) for the phosphorus trichloride to be distilled off from the reaction mixture after termination of the reaction until establishment of a temperature of 120° to 140° C. in the residue.

The following Examples illustrate the invention

EXAMPLE 1

(Comparative Example)

A solution of 117 g (1 mol) methyl-dichlorophosphane in 663 g phosphorus trichloride was placed, and heated to 30° C., in a four-necked flask provided with an agitator, thermometer, reflux condenser and inlet. At that temperature, 86.4 g (1.2 mol) acrylic acid was added dropwise within 8 minutes and with agitation. Next, the whole was stirred for 3 hours at 30° C. After 5, 60 and 180 minutes, respectively, a specimen was taken and subjected to H-NMR-spectroscopy. The results obtained are indicated in the following Table.

TABLE

|  | 5 min | | 60 min | | 180 min | |
| --- | --- | --- | --- | --- | --- | --- |
|  | g | Mol | g | Mol | g | Mol |
| $CH_3PCl_2$ | 117 | 1 | 65 | 0.56 | 17.5 | 0.15 |
| $CH_2=CHCOOH$ | 86.4 | 1.2 | 30 | 0.4 | — | — |
| $ClCH_2CH_2COOH$ | — | — | 31 | 0.25 | 44.5 | 0.35 |
| $CH_3P(O)(Cl)CH_2CH_2COCl$ | — | — | 80.5 | 0.43 | 151 | 0.8 |
| $CH_2=CHCOCl$ | — | — | 12.5 | 0.14 | — | — |
| Conversion $CH_3PCl_2$ | 0% | | 44% | | 85% | |
| Conversion $CH_2=CHCOOH$ | 0% | | 66.6% | | 100% | |

Next, low-boiling matter, namely phosphorus trichloride (bulk quantity), methyldichlorophosphane and β-chloropropionic acid chloride were removed under water jet vacuum until a temperature of 120° C. was found to have been established in the residue. After cooling, 159 g of a viscous mass was obtained. $^1$H-NMR-spectroscopy indicated that 95 weight% was 2-chloroformylethylmethylphosphinic acid chloride. The yield was 79.9%, based on $CH_3PCl_2$ used, 94% based on $CH_3PCl_2$ which underwent conversion, or 66.6%, based on acrylic acid used.

The residue was admixed at 80° C. with 102 g (1 mol) acetic anhydride, whereby 2-chloroformylethylmethylphosphinic acid chloride underwent conversion to 2-methyl-2,5-dioxo-1-oxa-2-phospholane. Resulting acetyl chloride was distilled off, nitrogen was passed over 3 hours at 120°–130° C. through the residue, and the latter was distilled under vacuum. 100 g 2-methyl-2,5-dioxo-1-oxa-2-phospholane melting at 102°–103° C. was obtained at 165° to 180° C. under a pressure of 0.8 millibar. The yield was 76.6%, based on methyldichlorophosphane used, 88%, based on methyldichlorophosphane which underwent conversion, or 62%, based on acrylic acid used.

EXAMPLE 2

(Comparative Example)

A solution of 117 g (1 mol) methyldichlorophosphane in 663 g phosphorus trichloride was placed, and heated to 70° C., in a four-necked flask provided with an agitator, thermometer, reflux condenser and inlet. Next, 86.4 g (1.2 mol) acrylic acid was added dropwise within 15 minutes with agitation. Acrylic acid and methyldichlorophosphane were used in a molar ratio of 1.2:1. During the dropwise addition, the temperature initially dropped down to 63° C. A vigorous reaction which was accompanied by foaming and black coloration of the reaction product soon set in so that it was necessary for the flask to be cooled so as to maintain the 70° C. temperature. Methyldichlorophosphane was found to have extensively reacted, 5 minutes after the addition of acrylic acid. This was determined on a specimen by H-NMR-spectroscopy. Stirring was continued for a further 30 minutes at 70° C. Next, low boilers were distilled off under water jet vacuum until a temperature of 120° C. was found to have been reached in the residue. After cooling, 141 g of a black brown viscous mass was obtained. $^1$H-NMR-spectroscopy indicated that 79 weight% was 2-chloroformylethylmethylphosphinic acid chloride. The yield was 58.9% based on $CH_3PCl_2$ used, or 49% based on acrylic acid used.

The residue was converted to 2-methyl-2,5-dioxo-1-oxa-2-phospholane, as described in Example 1. 77 g was obtained. The yield was 57.5% based on methyldichlorophosphane used, or 47.9% based on acrylic acid used.

EXAMPLE 3

The reaction was effected at 70° C. as described in Example 2, but a constant stream of hydrogen chloride of 10 l/h (=0.4 mol HCl per mol $CH_3PCl_2$ per hour) was passed through the reaction mixture over a period of altogether 45 minutes (addition of acrylic acid and post-reduction). The reaction solution remained colorless. The whole was worked up as described in Example 1 and 185.4 g of almost colorless crystalline matter melting at 59° C. was obtained. $^1$H-NMR-spectroscopy indicated that 99 weight% was 2-chloroformylethylmethylphosphinic acid chloride. The yield was 97.1% based on $CH_3PCl_2$ used, or 80.9%, based on acrylic acid used.

The residue was reacted as described in Example 1 and 128.5 g of 2-methyl-2,5-dioxo-1-oxa-2-phospholane melting at 103° C. was obtained. The yield was 95.9% based on methyldichlorophosphane used, or 79.9% based on acrylic acid used.

EXAMPLE 4

The procedure was as in Example 3, but 79.2 g (1.1 mol) acrylic acid was used. Acrylic acid and methyldichlorophosphane were used in a molar ratio of 1.1:1. The low boiler distillate of the reaction product was 648.5 g. It was analyzed by gas chromatography. It contained 99.1 weight% $PCl_3$, 0.6 weight% $CH_3PCl_2$ and 0.4 weight% $ClCH_2CH_2COCl$.

The $CH_3PCl_2$ conversion rate was 96.7%. The almost colorless solid residue (184.5 g) had a melting point of 59° C. $^1$H-NMR-spectroscopy indicated that 99 weight% was 2-chloroformylethylmethylphosphinic acid chloride. The yield was 96.6% based on $CH_3PCl_2$ used, 99.9% based on $CH_3PCl_2$ which underwent conversion, or 87.9% based on acrylic acid used.

The residue was reacted as described in Example 1 and 128.5 g 2-methyl-2,5-dioxo-1-oxa-2-phospholane was obtained. The yield was 95.9% based on $CH_3PCl_2$ used, 99.1% based on methyldichlorophosphane which underwent conversion, or 87.2% based on acrylic acid used.

EXAMPLE 5

A solution of 117 g (1 mol) methyldichlorophosphane in 663 g phosphorus trichloride through which 5 l/h hydrogen chloride (=0.2 mol HCl per mol $CH_3PCl_2$ per hour) was passed, was heated to boiling in the apparatus described in Example 1. A reflux temperature of 74° C. was found to establish. Metered into the boiling solution, within 30 minutes, was 75.6 g (1.05 mol) acrylic acid (acrylic acid and methyldichlorophosphane were used in a molar ratio of 1.05:1). The reflux temperature initially dropped down to 67° C. and then increased to 76° C. towards the end of the reaction. At that temperature, the reaction mixture was stirred for a further 30 minutes, while further hydrogen chloride was passed therethrough.

Next, the low boilers were distilled as described in Example 1 and 654.5 g distillate was obtained. It contained 99.5 weight% $PCl_3$, 0.3 weight% $CH_3PCl_2$ and less than 0.1 weight% β-chloropropionic acid chloride. The $CH_3PCl_2$-conversion rate was 98.3%. 183 g of almost colorless crystalline matter melting at 59°–60° C. was obtained as residue. $^1$H-NMR-spectroscopy indicated that 99 weight% was 2-chloroformylethylmethylphosphinic acid chloride.

The yield was 95.8% based on $CH_3PCl_2$ used, 97.5% based on $CH_3PCl_2$ which underwent conversion, or 91.3%, based on acrylic acid used.

The residue was reacted as in Example 1. 127.5 g 2-methyl-2,5-dioxo-1-oxa-2-phospholane melting at 103° C. was obtained. The yield was 96.8% based on methyldichlorophosphane which underwent conversion or 90.6% based on acrylic acid used.

EXAMPLE 6

This Example was carried out in continuous manner. The feed solution was a crude product such as that obtained in the production of methyldichlorophosphane from phosphorus trichloride and methane (cf. German Pat. No. 2 718 391) and used, inter alia, for the production of pure methyldichlorophosphane (cf. German Pat. "Auslegeschrift" No. 2 724 407). The crude product had the following composition, in weight%:

$CH_3PCl_2$: 15.4%
$PCl_3$: 79.7%
$CCl_4$: 2.8%
$HCCl_3$: 1.5%
$POCl_3$: 0.3%
not identified: 0.3%

A circulation evaporator which had a reaction volume of 1.1 liter and was comprised of two jacketed tubes in upright position and connected together at their upper and lower ends was used. It was filled with reaction product from a previous batch. The whole was heated to 74° C. so as to have a slight reflux in a reflux condenser positioned near the upper end of one of the two tubes. Introduced from below into the tube which had the reflux condenser connected thereto was 10 l/h hydrogen chloride gas (=0.13 mol HCl per mol $CH_3PCl_2$ per hour) to effect circulation of the material through the apparatus. The hydrogen chloride gas was removed through the reflux condenser.

Next, 206 g/h acrylic acid and 2300 g/h of the above crude product which contained 15.4 weight% methyldichlorophosphane were continuously admitted from below. This corresponded to the use of 2.86 mols/h acrylic acid and 354 g/h=3.02 mols methyldichlorophosphane. Acrylic acid and methyldichlorophosphane were used in a molar ratio of 0.95:1.

2505 g/h reaction product was taken continuously through an overflow. Altogether 50.1 kg was obtained after operation for 20 hours. In a continuously operated distilling apparatus, the reaction product was freed under atmospheric pressure from low boilers. Material in the circulation evaporator was kept under circulation by means of a stream of hydrogen chloride gas which was admitted at the rate of 5 l/h. 2-chloroformylethylmethylphosphinic acid chloride was continuously taken from the evaporator at 130° to 140° C. in the evaporator's base portion and collected. Altogether 39.05 kg of low boilers composed as follows were obtained:

$CH_3PCl_2$: 1.36%
$PCl_3$: 92.94%
$CCl_4$: 3.3%
$HCCl_3$: 1.74%
$POCl_3$: 0.35%
not identified: 0.35%

The distillate was recycled to the apparatus used for making methyldichlorophosphane from $PCl_3$ and $CH_4$. 10.52 kg 2-chloroformylethylmethylphosphinic acid chloride melting at 59°-60° C. was obtained as the distillation residue. $^1$H-NMR-spectroscopy indicated that the product had a purity of 99%. The yield was 91% based on $CH_3PCl_2$ used, 98.4% based on $CH_3PCl_2$ which underwent conversion, or 96.3% based on acrylic acid used.

The space/time-yield of 2-chloroformylethylmethylphosphinic acid chloride in the reactor was about 500 g. liter$^{-1}$·h$^{-1}$.

The residue was admixed at 70°-80° C. with 6250 g acetic anhydride, resulting acetyl chloride was distilled off, nitrogen gas was passed through the residue for 3 hours at 140° to 150° C. under a pressure of 70 to 140 millibars, and the residue was distilled under vacuum.

7240 g 2-methyl-2,5-dioxo-1-oxa-2-phospholane melting at 103° C. was obtained at 165° to 180° C. under 0.8 millibar.

The yield was 96.5% based on methyldichlorophosphane which underwent conversion, or 94.7% based on acrylic acid used.

We claim:

1. A process for making 2-chloroformylethylmethylphosphinic acid chlorides of the general formula:

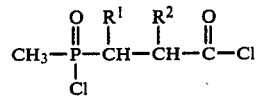

in which $R^1$ and $R^2$ each stand for hydrogen or $CH_3$, by reacting methyldichlorophosphane with an α,β-unsaturated carboxylic acid selected from the group consisting of acrylic acid, methacrylic acid or crotonic acid at elevated temperatures, which comprises: using a solution of methyldichlorophosphane in phosphorus trichloride, the solution originating from a reaction of phosphorus trichloride with methane at temperatures higher than 500° C.; effecting the reaction at temperatures within the range 50° to 90° C. in the presence of hydrogen chloride; and distilling off the phosphorus trichloride.

2. A process as claimed in claim 1, wherein a solution of methyldichlorophosphane in phosphorus trichloride containing 5 to 95 weight% of methyldichlorophosphane is used.

3. A process as claimed in claim 1, wherein 0.01 to 1 mol of hydrogen chloride per mol of methyldichlorophosphane per hour is passed through the reaction mixture.

4. A process as claimed in claim 1, wherein the reaction is effected at temperatures within the range 70° to 76° C.

5. A process as claimed in claim 1, wherein methyldichlorophosphane and α,β-unsaturated carboxylic acid are used in a molar ratio of 1:08-1.2.

6. A process as claimed in claim 1, wherein, after termination of the reaction, phosphorus trichloride is distilled off from the reaction mixture until establishment of a temperature of 120°-140° C. in the residue.

* * * * *